(12) United States Patent
Martínez Rovira et al.

(10) Patent No.: US 12,297,111 B2
(45) Date of Patent: May 13, 2025

(54) GRAPHENE PRODUCT AND THERAPEUTIC USES THEREOF

(71) Applicant: GRAPHENANO MEDICAL CARE, S.L., Madrid (ES)

(72) Inventors: Martin Martínez Rovira, Yecla-Murcia (ES); José Antonio Martínez Rovira, Yecla-Murcia (ES); María Del Prado Lavín López, Yecla-Murcia (ES); Amaya Romero Izquierdo, Ciudad Real (ES); Manuel Rodríguez Puyol, Madrid (ES); Diego Rodríguez Puyol, Madrid (ES); Sergio De Frutos García, Madrid (ES); Mercedes Griera Merino, Madrid (ES); Marco Antonio Hatem Vaquero, Madrid (ES); Ana Isabel Orozco Agudo, Madrid (ES)

(73) Assignee: GRAPHENANO MEDICAL CARE, S.L., Madrid (ES)

( * ) Notice: Subject to any disclaimer, the term of this patent is extended or adjusted under 35 U.S.C. 154(b) by 855 days.

(21) Appl. No.: 17/258,815

(22) PCT Filed: Jul. 17, 2019

(86) PCT No.: PCT/EP2019/069288
§ 371 (c)(1),
(2) Date: Jan. 8, 2021

(87) PCT Pub. No.: WO2020/016324
PCT Pub. Date: Jan. 23, 2020

(65) Prior Publication Data
US 2021/0292171 A1    Sep. 23, 2021

(30) Foreign Application Priority Data

Jul. 17, 2018  (EP) .................................... 18382531

(51) Int. Cl.
| | |
|---|---|
| *C01B 32/19* | (2017.01) |
| *A61K 9/00* | (2006.01) |
| *A61K 9/06* | (2006.01) |
| *A61K 33/44* | (2006.01) |
| *A61P 17/02* | (2006.01) |
| *B82Y 5/00* | (2011.01) |
| *B82Y 40/00* | (2011.01) |

(52) U.S. Cl.
CPC ............ *C01B 32/19* (2017.08); *A61K 9/0014* (2013.01); *A61K 9/06* (2013.01); *A61K 33/44* (2013.01); *A61P 17/02* (2018.01); *B82Y 5/00* (2013.01); *B82Y 40/00* (2013.01); *C01P 2002/01* (2013.01); *C01P 2002/74* (2013.01); *C01P 2002/82* (2013.01); *C01P 2004/03* (2013.01); *C01P 2004/04* (2013.01); *C01P 2004/51* (2013.01); *C01P 2004/61* (2013.01); *C01P 2006/12* (2013.01); *C01P 2006/14* (2013.01); *C01P 2006/80* (2013.01)

(58) Field of Classification Search
CPC ....... C01B 32/19; A61P 17/02; A61K 9/0014; A61K 9/06; A61K 33/44; B82Y 5/00; B82Y 40/00; C01P 2002/01; C01P 2002/74; C01P 2002/82; C01P 2004/03; C01P 2004/04; C01P 2004/51; C01P 2004/61; C01P 2006/12; C01P 2006/14; C01P 2006/80
See application file for complete search history.

(56) References Cited

U.S. PATENT DOCUMENTS

| | | |
|---|---|---|
| 2006/0134096 A1 | 6/2006 | Petrik |
| 2014/0120081 A1 | 5/2014 | Tour et al. |

FOREIGN PATENT DOCUMENTS

| | | |
|---|---|---|
| EP | 3 130 353 A1 | 2/2017 |
| GB | 2532449 A | 5/2016 |
| KR | 20170106062 A | 9/2017 |
| WO | 2015/034930 A1 | 3/2015 |

OTHER PUBLICATIONS

International Search Report of PCT/EP2019/069288, mailed Sep. 13, 2019.
Written Opinion of the International Searching Authority of PCT/EP2019/069288, mailed Sep. 13, 2019.
International Search Report of PCT/EP2019/069282, mailed Sep. 13, 2019.
Written Opinion of the International Searching Authority of PCT/EP2019/069282, mailed Sep. 13, 2019.
Lingling Ou et al, "Toxicity of graphene-family nanoparticles: a general review of the origins and mechanisms", Particle and Fibre Toxicology,vol. 13, No. 1, Oct. 31, 2016 (Oct. 31, 2016), p. 1-24, XP055534278.
Sangiliyandi Gurunathan et al, "Synthesis, toxicity, biocompatibility, and biomedical applications of graphene and graphene-related materials", International Journal of Nanomedicine,vol. 11, May 1, 2016 (May 1, 2016), p. 1927-1945, XP055534241.
Xiaoqing Guo et al, "Assessment of the toxic potential of graphene family nanomaterials", Journal of Food and Drug Analysis,vol. 22, No. 1, Mar. 1, 2014 (Mar. 1, 2014), p. 105-115, XP055534330.
Mohamed H. Lahiani et al, "Graphene and carbon nanotubes activate different cell surface receptors on macrophages before and after deactivation of endotoxins : Activation of macrophages before and after deactivation of endotoxin", Journal of Applied Toxicology. ,vol. 37, No. 11, Nov. 1, 2017 (Nov. 1, 2017), p. 1305-1316, XP055534313.

(Continued)

*Primary Examiner* — Robert A Wax
*Assistant Examiner* — Olga V. Tcherkasskaya
(74) *Attorney, Agent, or Firm* — Collard & Roe, P.C.

(57) ABSTRACT

A graphene product obtained from Graphene Nanofibers (GNFs), having a modified crystal structure and a defined size distribution. The product is non-toxic and has useful biological properties such as wound healing and improving skin appearance. The product can be used in therapy.

13 Claims, 7 Drawing Sheets

(56) References Cited

OTHER PUBLICATIONS

Martin-Gullon I et al, "Differences between carbon nanofibers produced using Fe and Ni catalysts in a floating catalyst reactor", Jul. 1, 2006 (Jul. 1, 2006), vol. 44, No. 8, p. 1572-1580, XP025010855.
Sutter, P., Epitaxial graphene: How silicon leaves the scene. Nature Materials, 2009. 8(3): p. 171-172.
Jacobberger, R.M., et ah, Simple Graphene Synthesis via Chemical Vapor Deposition. Journal of Chemical Education, 2015. 92(11): p. 1903-1907.
Lavin-Lopez, M.P., et al., Thickness control of graphene deposited over polycrystalline nickel. New Journal of Chemistry, 2015. 39(6): p. 4414-4423.
Geim, A.K. and K.S. Novoselov, The rise of graphene. Nature Materials, 2007. 6(3): p. 183-191.
Lotya, M., et al., Liquid phase production of graphene by exfoliation of graphite in surfactant/water solutions. Journal of the American Chemical Society, 2009. 131(10): p. 3611-3620.
Zhang, L., et al., A review: Carbon nanofibers from electrospun polyacrylonitrile and their applications. Journal of Materials Science, 2014. 49(2): p. 463-480.
Andrea Francesco Verre et al, "Improving the glial differentiation of human Schwann-like adipose-derived stem cells with graphene oxide substrates", Interface Focus,vol. 8, No. 3, Jun. 6, 2018 (Jun. 6, 2018), p. 1-7, XP055535044.

Luo L., Liu M.; Adipose tissue in control of metabolism. J Endocrinol. Dec. 2016;23I(3):R77-R99.
Jung, U.J. and Choi, M.S. Obesity and its metabolic complications: the role of adipokines and the relationship between obesity, inflammation, insulin resistance, dyslipidemia and nonalcoholic fatty liver disease. Int J Mol Sci. Apr. 11, 2014; 15(4):6184-223.
Armoni, M. et al. Transcriptional regulation of the GLUT4 gene: from PPAR-gamma and FOXOI to FFA and inflammation. Trends Endocrinol Metab. Apr. 2007; 18(3): 100-7.
Gao, X. et al. Decreased lipogenesis in white adipose tissue contributes to the resistance to high fat diet-induced obesity in phosphatidylethanolamine N-methyltransferase-deficient mice. Biochimica et Biophysica Acta 1851 (2015) 152-162.
Bennet NT et al, Growth Factors and Wound Healing Part II, Role in Normal and Chronic wound Healing, Am J Surg 1993;166:74-81.
Wong VW et al, Surgical Approaches to Create Murine Models of Human Wound Healing, J Biomed Biotechnol. 2011 :969618, 8 pages.
X.J. Yang, et al, Swelling Behaviour and Elastic Properties of Gelatin Gels, Polym. Int. 44 (1997) 448-452.
Saponaro C et al.,The Subtle Balance between Lipolysis and Lipogenesis: A Critical Point in Metabolic HomeostasisNutrients 2015, 7, 9453-9474.
Tontonoz P. et al. Fat and Beyond: The Diverse Biology of PPAR°, Annu. Rev. Biochem. 2008. 77:289-312.

GRAPHENE PRODUCT AND THERAPEUTIC USES THEREOF

CROSS REFERENCE TO RELATED APPLICATIONS

This application is the National Stage of PCT/EP2019/069288 filed on Jul. 17, 2019 which claims priority under 35 U.S.C. § 119 of European Application No. 18382531.4 filed on Jul. 17, 2018, the disclosure of which is incorporated by reference. The international application under PCT article 21 (2) was published in English.

FIELD OF THE INVENTION

The invention relates to new graphene products, their compositions and their use in therapy.

BACKGROUND OF THE INVENTION

The family of graphene-based or graphene-related materials recently stepped into the spotlight after the 2010 Nobel Prize in Physics, and subsequent explosion in development of numerous applications for these materials in energy, electronics, sensors, light processing, medicine, and environmental fields. Graphene, the "founding" member of this family, is a two-dimensional material made of $sp^2$-hybridized carbon atoms arranged in a hexagonal honeycomb lattice.

The extended family of graphene-related materials includes graphene (single- and multi-layered), graphite, polycyclic aromatic hydrocarbons, carbon nanotubes, fullerenes, various graphene nanostructures of different dimensionalities (e.g., graphene nanofibers, graphene nanoparticles, graphene quantum dots, graphene nanoribbons, graphene nanomeshes, graphene nanodisks, graphene foams, graphene nanopillars), any combinations of other graphene-related materials, substituted graphene-related materials (e.g., the substitution of carbon atoms with N, B, P, S, Si, or others), and graphene-related materials functionalized with reactive functional groups (e.g., carboxyl groups, esters, amides, thiols, hydroxyl groups, diol groups, ketone groups, sulfonate groups, carbonyl groups, aryl groups, epoxy groups, phenol groups, phosphonic acids, amine groups, porphyrin, pyridine, polymers and combinations thereof).

Several publications describe the use of graphene materials for medical applications.

US2006/0134096 describes compositions and methods for medical use of graphene containing compositions, in particular non-porous carbon, other than fullerene or nanotubes, comprising graphene. They are used topically on wounds, as sorbent for toxins or in hemodialysis.

EP 3 130 353 discloses graphene nanostructure-based pharmaceutical compositions for preventing or treating neurodegenerative diseases. The graphene nanostructure inhibits fibril formation caused by protein misfolding.

US2014/0120081 discloses the use of carbon nanomaterials to treat oxidative stress in a subject by reducing the level of reactive oxygen species. The carbon nanomaterial is selected from nanotubes, graphene, graphene nanoribons, graphite, graphite oxide, etc. that can be functionalized.

GB2532449 describes functionalised nanomaterial for use in the treatment, prophylaxis, or prevention of cancer by inhibiting proliferation of cancer stem cells, wherein the nanomaterial is mono-layer graphene, few-layer graphene, nano-graphite, single-wall or multi-wall carbon nanotubes, fullerenes, carbon nanohorns, carbon nanofibres, or amorphous or partially amorphized nanocarbons or mixtures thereof. Graphene oxide is preferred.

Guranathan S. and Kim J-H. in International Journal of Nanomedicine, 2016:11, pages 1927-1945 review the synthesis, toxicity, biocompatibility and biomedical applications of graphene and graphene-related materials. As discussed in this document, many of these products still present problems of associated toxicity and biocompatibility. The toxic effect of graphene can be influenced by physicochemical properties such as size and distribution, surface charge, surface area, layer number, lateral dimensions, surface chemistry, purity, particulate state, surface functional groups and shape. Anticancer therapy, photo-thermal therapy, drug delivery, gene transfection, biosensing, imaging and tissue engineering are among the biomedical applications mentioned in this review.

There is still a need for new graphene based materials with low or no toxicity, good biocompatibility and able to provide a useful biological effect and applications in therapy.

BRIEF DESCRIPTION OF THE INVENTION

We have now found new graphene products having remarkable properties, with very low to no toxicity, and which are useful in therapy.

In a first aspect, the invention is directed to a graphene nanomaterial selected from graphene nanofibers, wherein the graphene nanomaterial has a particle size distribution having a dn(90) of 0.60 µm or smaller in number of particle and a dv(90) of 80.00 µm or smaller in volume particle, as measured by laser diffraction particle analyzer.

Preferably, the specific surface area of the graphene nanomaterial is comprised between 100 and 500 $m^2/g$, more preferably between 300-350 $m^2/g$ as measured by Brunnauer-Emmet-Teller ("BET") method.

In another embodiment, the pore volume of the graphene nanomaterial is between 0.35-0.40 $cm^3/g$.

It is also preferred that the impurities in the graphene nanomaterial are less than 0.01% by weight.

In another aspect, the invention is directed to a graphene nanomaterial as defined above for use as a medicament. In one embodiment, the medicament is for the treatment of wounds, eczema, psoriasis, scars, ulcers and other conditions which result in a disruption of the skin integrity.

In another aspect, the invention is directed to pharmaceutical compositions comprising the above defined graphene nanomaterial.

In a further aspect, the invention is directed to the use of the above defined graphene nanomaterial in therapy

DETAILED DESCRIPTION OF THE INVENTION

Graphene Raw Materials

In the present invention, the term "graphene" refers to a material forming a polycyclic aromatic molecule with multiple carbon atoms covalently bonded to each other. The covalently bonded carbon atoms forma six-member ring as a repeating unit.

The term "Graphene nanofibers" (GNFs) refers to cylindric nanostructures with graphene layers arranged as stacked cones, cups or plates. The graphene plane surface is canted from the fiber axis, which exposes the plane edges present on the interior and exterior surfaces of the carbon nanofibers.

The term "graphene nanotubes" (GNTs) refers to single wall or multi-wall concentric cylinders of graphene where the basal planes form a less reactive surface compared to that of Graphene Nanofibers because they are cylindrical and hollow like a tube but graphene nanofibers are like rods and generally there is no inner empty space within them.

The product of the invention is a carbon-based nanomaterial derived from GNF that is subjected to a series of purifications and treatments to obtain a medical grade material having unexpected biological properties.

The starting carbon nanomaterial is a graphene-based material (graphene nanofibers). In one embodiment, the graphene nanofibers used to prepare the product of the invention have a particle size distribution dn(90) of 4.0 μm or smaller for number of particle and a dv(90) of 105.00 μm or smaller for volume particle. Preferably they have a surface area of about 250-400 $m^2/g$.

Raw materials used to obtain the product of the invention can be synthesized following a wide variety of methods, such as epitaxial growth on silicon carbide, chemical vapor deposition, micromechanical or mechanical exfoliation of graphite, chemical oxidation of graphite, reduction of graphite oxide using thermal, chemical or multistep reduction, catalysis decomposition of hydrocarbons over metal catalyst, unrolling carbon nanotubes, electrospinning, etc.

Epitaxial growth on silicon carbide is a method in which monolayers isolated from graphene can be synthesized on a monocrystalline silicon carbide crystal (SiC), which is used as a substrate. This method consists of heating SiC wafers to high temperatures (>1100° C.) and high vacuum. Under the conditions mentioned, the silicon atoms sublime obtaining the epitaxial growth of graphene on its surface (the carbon atoms rearrange themselves forming graphene) [Sutter, P., Epitaxial graphene: How silicon leaves the scene. Nature Materials, 2009. 8 (3): p. 171-172.]

In the Chemical Vapor Decomposition method, a carbon source decays catalytically on a catalytic substrate. The catalytic surface causes, after the thermal decomposition of the hydrocarbons, the dissolution of the carbon atoms generated inside the metal [Jacobberger, R. M., et al., Simple Graphene Synthesis via Chemical Vapor Deposition. Journal of Chemical Education, 2015. 92 (11): p. 1903-1907, Lavin-Lopez, M. P., et al., Thickness control of graphene deposited over polycrystalline nickel. New Journal of Chemistry, 2015. 39 (6): p. 4414-4423].

The micromechanical exfoliation of graphite consists in the separation of the outermost layer of said solid in flakes by means of fine scraping, using a solid surface object or adhesive tape [Geim, A. K. and K. S. Novoselov, The rise of graphene. Nature Materials, 2007. 6 (3): p. 183-191]. The mechanical exfoliation allows separating the sheets that form the suspended graphite in organic or aqueous solvents by means of ultrasound waves. The material obtained is of high quality, however, it is not of great industrial interest given its low yield and its high production cost [Lotya, M., et al., Liquid phase production of graphene by exfoliation of graphite in surfactant/water solutions. Journal of the American Chemical Society, 2009. 131 (10): p. 3611-3620].

A wide variety of methods can also be used to synthesize graphene nanofibers (GNFs), which are especially preferred to prepare the product of the invention. For example, the Chemical Vapor Deposition method for carbon nanofiber is a catalytic method in which a carbonaceous source is decomposed in the presence of a catalyst to grown GNFs. Transition metal catalytic particles such as iron, nickel, cobalt, and copper are used as catalyst. CVD process takes place at temperatures ranging between 500 to 1200° C. [Martin-Gullon, I., et al., Differences between carbon nanofibers produced using Fe and Ni catalysts in a floating catalyst reactor. Carbon, 2006. 44 (8): p. 572-1580]. Electrospinning is an alternative production method of GNFs. In this method, the sol—gel process is used needing—a needle with a fine tip. For this, high voltage is applied to the drop of the needle, causing the solution to come out of the needle towards a target. When the surface tension is high enough for the solution, avoid entering a fine drop, a fibrous structure can be extracted and collected in the objective [Zhang, L., et al., A review: Carbon nanofibers from electrospun polyacrylonitrile and their applications. Journal of Materials Science, 2014. 49 (2): p. 463-480].

The average diameters and lengths of the porous graphitic material which are used to prepare the composite of the invention are measured by Transmission Electron Microscopy (TEM).

Purification and Treatment

A graphene nanomaterial synthesized following the methods reported above is used as raw material to synthesize the graphene-based medical grade material of the invention. The raw graphene nanomaterial is then subjected to a purification process, preferably using a strong acid ($H_2SO_4$, HCl, HF, $HNO_3$, HBr, etc.), to remove any metal or impurity introduced in the graphene nanomaterial structure during the synthesis process. Any process able to remove impurities without affecting the properties of the graphene material can be used. Among the acids, hydrochloric or fluorhydric acid are especially preferred, but the skilled person will select the acid and conditions depending on the amount and type of impurities present. The purification process preferably takes place at low temperatures (20-50° C.) for several hours (12-24 hours). If a solution is used for the purification process, the purified graphene nanomaterial can then be washed with Millipore water until neutral pH and then dried, for example vacuum dried.

The purified graphene nanomaterial is also treated to achieve a reduced particle size distribution, which makes the product suitable for medical and cosmetic uses. The purified graphene nanomaterial is for example subjected to a process to reduce its size and modify its properties. In one embodiment it is subjected to an exfoliation process at room temperature, for example through ultrasonication, wet milling or hybrid processes. Ultrasonication is especially preferred due to the simplicity of the process, which additionally can be monitored through samples to check if the desired particle size distribution is achieved. After that, an optional delimitation process to control the particle size between 10-100 μm takes place. The skilled person will readily determine the technique required to select the particle size distribution. For example, this step can be achieved by means of filtration or centrifugation, preferably vacuum filtration, for example through sintered glass filter. Said delimitation step can advantageously lead to particles having a dn(90) of 0.60 μm or smaller in number of particle and a dv(90) of 80.00 μm or smaller in volume particle.

Finally, to control that the grade material is not dragging traces of other toxic compounds, including bacteriological contamination or endotoxins and in order to maintain asepsis and sterility conditions, the material can also be subjected to a standard depyrogenization process by heat, preferably at 200-500° C. for 10-60 min.

The resulting particle size distribution can be determined by common means in the field, such as a particle size analyser, for example, a Mastersizer 2000 from Malvern Pananalytical as used in the examples.

Therefore, a further object of the invention is a method to prepare the product of the invention from raw graphene nanofibers, comprising the following steps:
a) Purifying the raw graphene material, preferably using a strong acid, to remove any metal or impurity present in the graphene raw material,
b) Reducing the particle size of the purified graphene nanomaterial, preferably through an exfoliation process, to a particle size distribution having a dn(90) of 0.60 μm or smaller in number of particle and a dv(90) of 80.00 μm or smaller in volume particle, as measured by laser diffraction particle analyzer,
c) Optionally subjecting the obtained product to a depyrogenization process.

Step (b) can further comprise the step of delimiting the particles according to the particle size before step (c). In one embodiment, the delimitation step is achieved by filtration or centrifugation, preferably vacuum filtration.

In the context of the present invention, a particle size distribution having a dn(90) of 0.60 μm or smaller in number of particle and a dv(90) of 80.00 μm or smaller in volume particle can be obtained by following step (b), optionally including the further delimiting step, preferably a filtration step. Preferably, the filtration is vacuum filtration with a sintered glass filter of pore size comprised between 1 and 20 μm, preferably between 4 and 20 μm, more preferably between 5 and 16 μm.

Product

The product of the invention is a purified graphene nanomaterial with a particle size distribution having a dn(90) of around 0.60 μm of smaller in number of particle and a dv(90) of 80.00 μm or smaller, preferably 70.00 μm or smaller in volume particle.

The particle size distribution is measured by a laser diffraction particle size analyzer. A particle Size Distribution D50 is the value of the particle diameter at 50% in the cumulative distribution. If D50 has a certain value, then 50% of the particles in the sample are larger than this value and 50% are smaller. The particle size distribution is the number of particles that fall into each of the various size ranges given as a percentage of the total number of all sizes in the sample of interest. The most widely used method of describing particle size distributions are d values (d10, d50 and d90) which are the intercepts for 10%, 50% and 90% of the cumulative mass.

These values can be thought of as the diameter of the material which divides the samples mass into a specified percentage when the particles are arranged on an ascending mass basis. The d10 is the diameter at which 10% of the sample's mass is comprised of particles with a diameter less than this value. The d50 is the diameter of the particle that 50% of a sample's mass is smaller than and 50% of a sample's mass is larger than d90 is the diameter at which 90% of the sample's mass is comprised of particles with a diameter less than this value. These values can be applied for number of particles (dn) and volume of particles (dv).

A distribution having a dn(90) in number of particle means the point in the size distribution, up to and including which, 90% of the total number of material in the sample is contained.

A distribution having a dv(90) in volume of particle means the point in the size distribution, up to and including which, 90% of the total volume of material in the sample is contained.

The particle size distribution of the product of the invention is measured with a Mastersizer 3000 of Malvern Panalytical.

In the context of the present invention, the term "specific surface area (SSA)" refers to the total surface area of a material per unit of mass.

The properties of porosity and specific surface area described in the present application are measured using Brunnauer-Emmet-Teller ("BET") methods, applied in physical adsorption technique using nitrogen as the adsorptive material, which is well known to the person skilled in the art.

In an embodiment of the invention, the BET surface area of the product of the invention is between 300-350 m$^2$/g.

In another embodiment, the pore volume of the product of the invention is between 0.35-0.40 cm$^3$/g.

In a preferred embodiment, the product of the invention has a BET surface area between 300-350 m$^2$/g and a pore volume between 0.35-0.40 cm$^3$/g.

The product of the invention is in the form of graphene nanofibers.

Composition

In another aspect, the invention relates to a pharmaceutical composition comprising the graphene product of the invention and one or more pharmaceutically acceptable excipients.

"Pharmaceutical composition" as used herein, relates to compositions and molecular entities that are physiologically tolerable and do not typically produce an allergic reaction or a similar unfavorable reaction as gastric disorders, dizziness and suchlike, when administered to a human or animal.

Preferably, the term "pharmaceutically acceptable" means it is approved by a regulatory agency of a state or federal government and/or is included in the European U.S. Pharmacopoeia and/or other generally 10 recognized pharmacopoeia for use in animals, and more particularly in humans.

The term "excipient" refers to a vehicle, diluent or adjuvant that is administered with the active ingredient. Such pharmaceutical excipients can be sterile liquids, such as water and oils, including those of petroleum, animal, vegetable or synthetic origin, such as peanut oil, soybean oil, mineral oil, sesame oil and similar.

In a preferred embodiment the pharmaceutical composition of the invention is suitable for topical administration to the skin, such as for example creams, lotions, ointments, microemulsions, fatty ointments, gels, emulsion-gels, pastes, foams, tinctures, solutions, patches, bandages and transdermal therapeutic systems. Most preferred are creams or emulsion-gels.

Creams or lotions are oil-in-water emulsions. Oily bases that can be used are fatty alcohols, especially those containing from 12 to 18 carbon atoms, for example lauryl, cetyl or stearyl alcohol, fatty acids, especially those containing from 10 to 18 carbon atoms, for example palmitic or stearic acid, fatty acid esters, e.g. glyceryl tricaprilocaprate (neutral oil) or cetyl palmitate, liquid to solid waxes, for example isopropyl myristate, wool wax or beeswax, and/or hydrocarbons, especially liquid, semi-solid or solid substances or mixtures thereof, for example petroleum jelly (petrolatum, Vaseline) or paraffin oil. Suitable emulsifiers are surface-active substances having predominantly hydrophilic properties, such as corresponding non-ionic emulsifiers, for example fatty acid esters of polyalcohols and/or ethylene oxide adducts thereof, especially corresponding fatty acid esters with (poly)ethylene glycol, (poly) propylene glycol or sorbitol, the fatty acid moiety containing especially from 10 to 18 carbon atoms, especially partial glycerol fatty acid esters or partial fatty acid esters of polyhydroxyethylene sorbitan, such as polyglycerol fatty acid esters or polyoxyethylene sorbitan fatty acid esters (T weens), and also polyoxyethylene fatty alcohol ethers or fatty acid esters, the fatty alcohol moiety containing especially from 12 to 18 carbon atoms and the fatty acid moiety especially from 10 to 18 carbon atoms, such as polyhydroxyethyleneglycerol fatty acid ester (for example Tagat S), or corresponding ionic emulsifiers, such as alkali metal salts of fatty alcohol sulfates, especially having from 12 to 18 carbon atoms in the fatty alcohol moiety, for example sodium lauryl sulfate, sodium cetyl sulfate or sodium stearyl sulfate, which are usually used in the presence of fatty alcohols, for example cetyl alcohol or stearyl alcohol. Additives to the aqueous phase are, inter alia agents that prevent the creams from drying out, for example humectants, such as polyalcohols, such as glycerol, sorbitol, propylene glycol and/or polyethylene glycols, and also preservatives, perfumes, gelling agents, etc.

Ointments are water-in-oil emulsions that contain up to 70%, but preferably from approximately 20% to approximately 50%, water or aqueous phase. Suitable as fatty phase are especially hydrocarbons, for example petroleum jelly, paraffin oil and/or hard paraffins, which, in order to improve the water-binding capacity, preferably contain suitable hydroxy compounds, such as fatty alcohols or esters thereof, for example cetyl alcohol or wool wax alcohols, or wool wax or beeswax. Emulsifiers are corresponding lipophilic substances, for example of the type indicated above, such as sorbitan fatty acid esters (Spans), for example sorbitan oleate and/or sorbitan isostearate. Additives to the aqueous phase are, inter alia humectants, such as polyalcohols, for example glycerol, propylene glycol, sorbitol and/or polyethylene glycol, and also preservatives, perfumes, etc.

Microemulsions are isotropic systems based on the following four components: water, a surfactant, for example a tensioactive, a lipid, such as a non-polar or polar oil, for example paraffin oil, natural oils such as olive or maize oil, and an alcohol or polyalcohol containing lipophilic groups, for example 2-octyldodecanol or ethoxalated glycerol or polyglycerol esters. If desired, other additives may be added to the microemulsions. Microemulsions have micelles or particles with sizes below 200 nm and are transparent or translucid systems, the form spontaneously and are stable. Fatty ointments are water-free and contain as base especially hydrocarbons, for example paraffin, petroleum jelly and/or liquid paraffins, also natural or partially synthetic fat, such as fatty acid esters of glycerol, for example coconut fatty acid triglyceride, or preferably hardened oils, for example hydrogenated groundnut oil, castor oil or waxes, also fatty acid partial esters of glycerol, for example glycerol mono- and di-stearate, and also, for example, the fatty alcohols increasing the water-absorption capacity, emulsifiers and/or additives mentioned in connection with the ointments.

In relation to gels, a distinction is made between aqueous gels, water-free gels and gels having a low water content, which gels consist of swellable, gel-forming materials. There are used especially transparent hydrogels based on inorganic or organic macromolecules. High molecular weight inorganic components having gel-forming properties are predominantly water-containing silicates, such as aluminium silicates, for example bentonite, magnesium aluminium silicates, sold under the trademark VEEGUM®, or colloidal silicic acid sold under the trademark AEROSIL®. As high molecular weight organic substances there are used, for example, natural, semisynthetic or synthetic macromolecules. Natural and semi-synthetic polymers are derived, for example, from polysaccharides containing a great variety of carbohydrate components, such as celluloses, starches, tragacanth, gum arabic and agar-agar, and gelatin, alginic acid and salts thereof, for example sodium alginate, and derivatives thereof, such as lower alkylcelluloses, for example methyl- or ethyl-cellulose, carboxy- or hydroxy-lower alkylcelluloses, for example carboxymethyl- or hydroxyethylcellulose. The components of synthetic gel-forming macromolecules are, for example, suitably substituted unsaturated aliphatic compounds such as vinyl alcohol, vinylpyrrolidine, acrylic or methacrylic acid.

Emulsion-gels—also called "emulgels"—represent topical compositions which combine the properties of a gel with those of an oil-in-water emulsion. In contrast to gels, they contain a lipid phase which due to its fat-restoring properties enables the formulation to be massaged in whilst, at the same time, the direct absorption into the skin is experienced as a pleasant property. Furthermore, one can observe an increased solubility for lipophilic active ingredients. One advantage of emulsion-gels over oil-in-water emulsions resides in the enhanced cooling effect which is brought about by the coldness due to evaporation of the additional alcohol component, if present.

Foams are administered, for example, from pressurised containers and are liquid oil-in water emulsions in aerosol form; unsubstituted hydrocarbons, such as alkanes, for example propane and/or butane, are used as propellant. As oil phase there are used, inter alia hydrocarbons, for example paraffin oil, fatty alcohols, for example cetyl alcohol, fatty acid esters, for example isopropyl myristate, and/or other waxes. As emulsifiers there are used, inter alia, mixtures of emulsifiers having predominantly hydrophilic properties, such as polyoxyethylene sorbitan fatty acid esters sold under the trademark TWEENS®, and emulsifiers having predominantly lipophilic properties, such as sorbitan fatty acid esters sold under the trademark SPANS®. The customary additives, such as preservatives, etc., are also added. Tinctures and solutions generally have an ethanolic base, to which water may be added and to which there are added, inter alia, polyalcohols, for example glycerol, glycols and/or polyethylene glycol, as humectants for reducing evaporation, and fat-restoring substances, such as fatty acid esters with low molecular weight polyethylene glycols, propylene glycol or glycerol, that is to say lipophilic substances that are soluble in the aqueous mixture, as a replacement for the fatty substances removed from the skin by the ethanol, and, if necessary, other adjuncts and additives. Suitable tinctures or solutions may also be applied in spray form by means of suitable devices.

Transdermal therapeutic systems with—in particular—local delivery of the graphene product of the invention contain an effective amount of the graphene product optionally together with a carrier. Useful carriers comprise absorbable pharmacological suitable solvents to assist passage of the active ingredient through the skin. Transdermal delivery systems are, for example, in the form of a patch comprising (a) a substrate (=backing layer or film), (b) a matrix containing the active ingredient, optionally carriers and optionally (but preferably) a special adhesive for attaching the system to the skin, and normally (c) a protection foil (=release liner). The matrix (b) is normally present as a mixture of all components or may consist of separate layers.

Membranes and matrixes comprising the graphene product of the invention are also suitable for the topical application of the product, either by themselves or as a part of a more complex product, such as a wound dressing, a bandage, etc. Example of such membranes or matrixes are natural polymers such as polysaccharides (alginates, chitin, chitosan, heparin, chondroitin, carrageenan), proteoglycans and proteins (collagen, gelatin, fibrin, keratin, silk fibroin, eggshell membrane); synthetic polymers such as hydrogels or biomimetic extracellular matrix micro/nanoscale fibers based on polyglycolic acid, polylactic acid, polyacrylic acid, poly-ε-caprolactone, polyvinylpyrrolidone, polyvinyl alcohol, polyethylene glycol, etc.

All these systems are well-known to the person skilled in the art. The manufacture of the topically administrable pharmaceutical preparation is effected in a manner known per se, for example by suspending the graphene product of the invention in the base or, if necessary, in a portion thereof.

The compositions according to the invention may also comprise conventional additives and adjuvants for dermatological applications, such as preservatives, especially paraben esters like methylparaben, ethylparaben, propylparaben, butylparaben, or quaternary ammonium compounds like benzalkonium chloride, or formaldehyde donors like imidazolidinyl urea, or alcohols like benzyl alcohol, phenoxyethanol or acids like benzoic acid, sorbic acid; acids or bases used as pH buffer excipients; antioxidants, especially phenolic antioxidants like hydroquinone, tocopherol and derivatives thereof, as well as flavonoids, or miscellaneous antioxidants like ascorbic acid, ascorbyl palmitate; perfumes; fillers such as kaolin or starch; pigments or colorants; UV-screening agents; moisturizers, especially glycerin, butylen glycol, hexylen glycol, urea, hyaluronic acid or derivatives thereof; anti-free radical agents such as vitamin E or derivatives thereof; penetration enhancers especially propylene glycol; ethanol; isopropanol; dimethylsulfoxide; N-methyl-2-pyrrolidone; fatty acids/alcohols such as oleic acid, oleyl alcohol; terpenes such as limonen, menthol, 1-8 cineole; alkyl esters such as ethyl acetate, butyl acetate; ion pairing agents such as salicylic acid.

Further details concerning suitable topical formulations may be obtained by reference to standard textbooks such as Remington "The science and practice of pharmacy" $22^{nd}$ Edition (2012).

The amount of the graphene nanomaterial product of the invention in the formulation can be in the range of 0.01% to 10% w/w, preferably from 0.01% to 5% w/w, more preferably from 0.1% to 3% w/w.

Beneficial Effects and Uses

As evidenced by the examples below, the product of the invention is not toxic, also when applied topically, and has good biocompatibility.

In addition, and surprisingly, the product of the invention has shown to be effective in skin repair and wound healing, as shown in the examples.

Therefore, the graphene product of the invention, and compositions containing it, are useful as medicament in therapy.

The term "therapy" or "therapeutic" is understood to mean treating or preventing disease in human beings or animals and restoring, correcting or modifying physiological functions in humans or in animals.

Many conditions may compromise the integrity of the skin and the dermal function, such as, diabetes mellitus, trauma, inflammatory diseases, metabolic abnormalities, bleeding disorders, autoimmune diseases such as psoriasis, between others. Therefore, promotion of skin lesion healing, regardless of the nature of the causative agent, is of utmost importance. After injury to skin, the wound closure is driven by the formation of new epithelium by proliferation and directional migration of different cell types such as keratinocytes or fibroblasts to wound edges. [Bennet N T et al., Am J Surg 1993; 166:74-81; Wong V W et al., J Biomed Biotechnol. 2011:969618.]

The graphene product of the invention has proved to be effective in the repair of wounds in a rat model, and to be harmless in terms of systemic changes of renal, hepatic or inflammatory markers in vivo.

Therefore it is useful in the treatment of any condition that results in a disruption of the skin integrity, such as wounds, scars, bums, ulcers, psoriasis, cuts or otherwise traumatised mammalian skin. Such lesions may be caused by a broad spectrum of events and/or may be associated with other diseases. The lesions to be treated include those associated with incision, laceration, abrasion, blister, hematoma, puncture, penetration, electricity, irradiation, chemical, trauma, crush, bite, bum, frost, surgery, primary cancer or metastasis, benign tumor, acne, infections such as bacterial infection (which may be combined with fungal or viral of parasitic infection), lesions associated with decreased circulation of blood, such as leg ulcers and foot ulcers associated with venous insufficiency or arterial insufficiency, decubitus ulcers, pressure sores or bedsores, and lesions associated with diabetes mellitus or psoriasis.

Mode of Administration

The composition used in the present method is preferably applied topically.

The daily dosage of the topical formulation comprising the graphene product of the invention may depend on various factors, such as sex, age, weight and individual condition of the patient.

EXAMPLES

Example 1

GMC-1 Preparation and Physico-Chemical Characterization

Raw Materials

The textural characteristics, the degree of graphitization, and the main physical-chemical and thermal properties of the raw materials that can be used to prepare the graphene nanomaterials of the invention are present in Table 1 below.

TABLE 1

Physico-chemical properties of raw GNFs

| Characteristics | Property | GNFs |
|---|---|---|
| Textural | Surface area (m²/g) | 250-400 |
| Graphitization degree | DRX: npg [a] (npg from graphite≈95) | 6-10 |
|  | RAMAN: $I_D/I_G$ ($I_D/I_G$ from graphite≈0.6) [b] | 1.0-1.4 |
| Physical and Chemical | Odour, colour and appearance | Without smell, black powder, spongy |
|  | Solid content | 100% |
|  | Solubility |  |
|  | Thermal conductivity (W/mK) | 1400-1600 |
| Thermal | Oxidation temperature (° C.) | 680 |
|  | Thermal decomposition/oxidation products | Principally CO and $CO_2$ |

[a] number of graphene planes in the crystal (npg = Lc/d); d is the interlaminate range; Lc is the average size of the crystal in the sample, in a perpendicular direction to the basal planes of graphene
[b] $I_D/I_G$: quotient between the intensities of D and G bands in the RAMAN spectrum.

In the present example graphene nanofibers (GNFs) have been used to prepare a material according to the invention.

The raw graphene-based carbon nanomaterial (GNFs) is subjected to a purification process using HF to remove metal and impurities introduced in the GNFs structure during the synthesis process. The purification process takes place at low temperatures (20-50° C.) for several hours (12-24 hours). After that the purified carbon nanomaterial is vacuum dried and washed with Millipore water until neutral pH.

The purified GNFs were then subjected to an exfoliation process for several hours (2-5 h) at room temperature in a solution with water or other solvents. Finally, the material is subjected to a standard depirogenization process by heat (200-500° C. for 10-60 min).

The resulting product (GMC-1) has been characterized as follows:

Elemental Analysis of GMC-1

The main difference between GMC-1 and the raw materials can be observed in their elemental analysis (Table 2). In comparison with the raw GNFs, GMC-1 is only composed of carbon and oxygen. It does not have any impurity traces that could be harmful to human health, as confirmed by toxicology experiments.

TABLE 2

Elemental analysis of raw CNFs and GMC-1

| Element | CNFs | GMC-1 |
|---|---|---|
| C | 80-90 | 92-95 |
| O | 10-15 | 5-6 |
| Impurity traces (metals, catalyst support, etc.) | 0.5-1.5 | 0.0-0.01 |

Raman Spectroscopy of GMC-1

Figure 1:
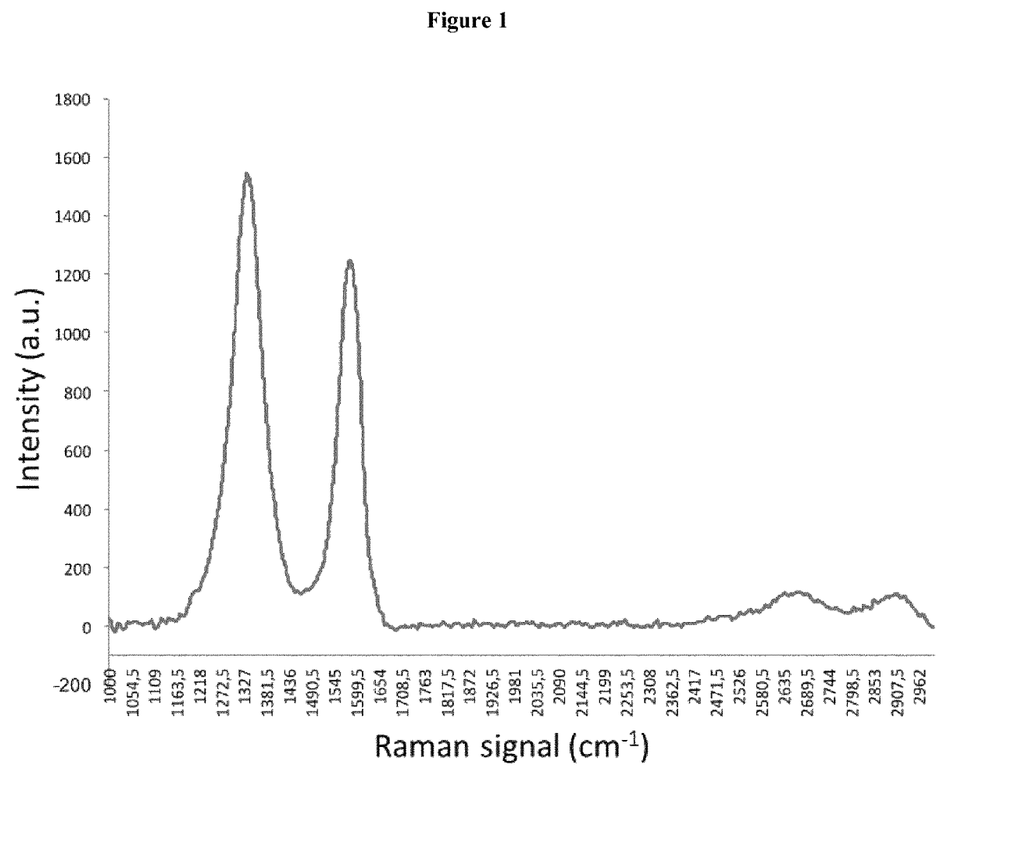
FIG. 1.—Raman spectroscopy of the graphene nanomaterial of the invention (GMC-1)

The Raman spectrum of GMC-1 was obtained using a 512 nm laser. It shows (FIG. 1) the characteristic peaks of coal materials. Peak D, 1332 cm⁻¹, and peak G, 1580 cm⁻¹. The G band corresponds to the networks of carbon atoms, that is, to the ideal graphitic structure, while the D band is due to the existence of defects, both in the basal plane and at the edges. Graphene nanofibers have a band D of great intensity, greater than the band G. A large D peak can appear in graphitic materials if they contain a large number of edges, as in the case of these nanofibers. The fact that both peak D and G do not have too high a bandwidth also shows the crystallinity of the nanofibers.

Absorption-Nitrogen Desorption Analysis of GMC-1

The basis for measuring the total surface area of a solid by physisorption of a gas is to detect the number of gas molecules needed to cover the surface of the solid. Once the area occupied by the molecule is known, the surface area of the solid can be estimated from the number of molecules of gas absorbed, measured volumetrically or gravimetrically (Brunauer, Emmett and Teller).

The total surface area was calculated by the multipoint BET equation, while the total pore volume was determined by the amount of vapor adsorbed at a relative pressure $P/P_0=0.99$, assuming that the pores are subsequently filled with liquid adsorbate. The average pore size, assumed to be cylindrical, was estimated from the total pore volume value and the surface area, assuming that pores that were not filled at relative pressures less than 1 did not contribute to the volume and surface area of the pore sample.

Figure 2:
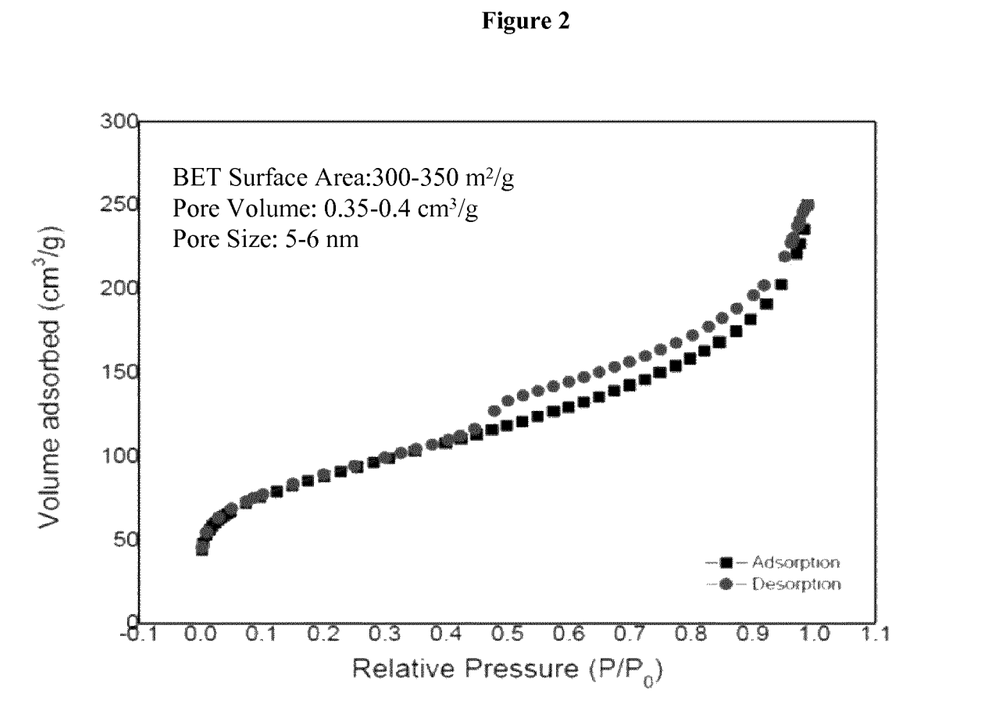
FIG. 2.—Adsorption—desorption in $N_2$ of GMC-1

The analysis of surface area, pore volume and pore area were made by adsorption-desorption of $N_2$ at 77 K, using a QUANTACHROM model QUADRASORB SI model, with six degassing ports and three analysis ports, controlled with software (QUADRAWIN) that collects the values of relative pressure for each volume of $N_2$ dosed. FIG. 2 shows the surface area, pore volume and pore size of GMC-1.

BET Surface Area: 300-350 m²/g

Pore Volume: 0.35-0.4 cm³/g

Pore Size: 5-6 nm

X-Ray Diffraction of GMC-1

Figure 3A:
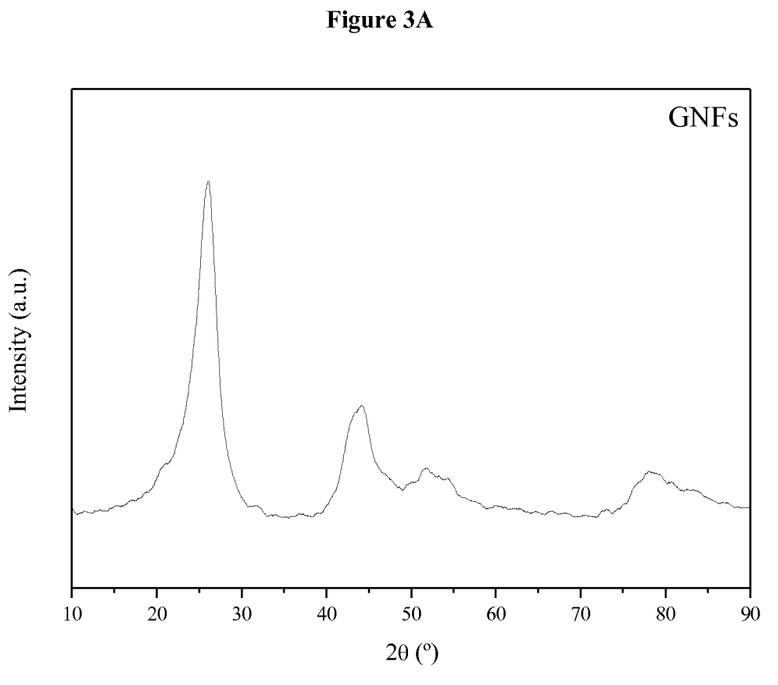
FIG. 3A.—X-Ray diffraction of graphene nanofibers (GNFs) raw material

X-Ray diffractogram corresponding to a sample of GNFs was performed (FIG. 3A). As it is observed, it presents a peak around 25.9° that corresponds to the distance between planes 002 of the graphite, or distance between the sheets of graphene. In the highly crystalline graphite, the interlaminar distance is 0.334 nm. In this case, the nanofibers have a slightly greater distance, 0.343 nm, which is indicative that they have a short-range crystallinity and are turbostratic. The crystal size in the direction perpendicular to the plane 002 (Lc) is 4.64 nm, indicative of the above mentioned fact.

Figure 3B:
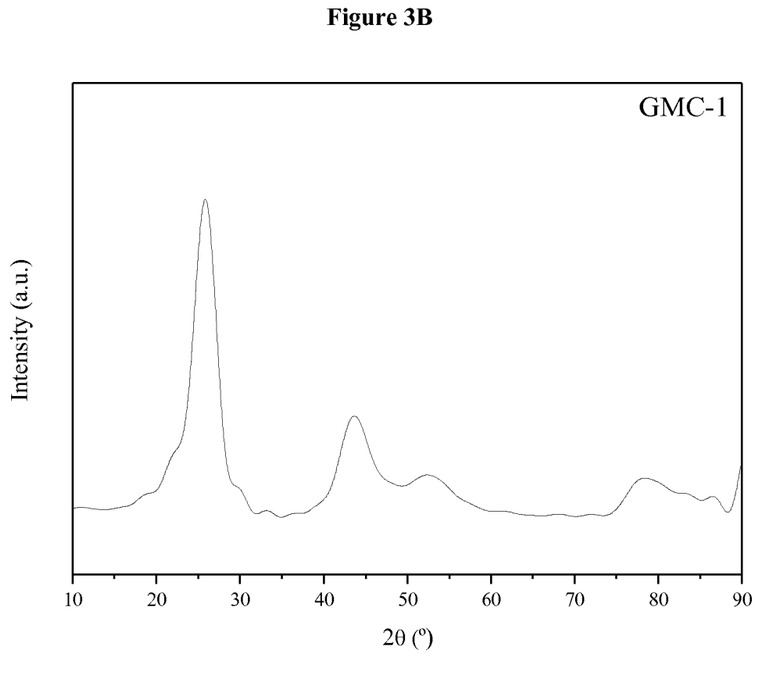
FIG. 3B.—X-Ray diffraction of GMC-1

FIG. 3B shows the diffractogram corresponding to a sample of the material according to the invention GMC-1. GNFs and GMC-1 presented the same peaks, however in GMC-1 these peaks presented lower value of 2θ.

Table 3 shows the characteristic crystallographic parameters for GNFs and GMC-1:

Interlaminar space (d002)

Crystal stack height (Lc)

In-plane crystallite size (La)

Number of graphene layers in the crystal (npg)

$$d = \frac{\lambda}{2 \cdot sen\theta_1}; L_c = \frac{k_1 \cdot \lambda}{FWHM \cdot cos\theta_1}; La(\text{nm}) = \frac{k_2 \cdot \lambda}{FWHM \cdot cos\theta_2}; npg = \frac{L_c}{d}$$

where:
- λ, radiation wavelength (λ=0.15404 nm)
- θ1, diffraction peak position (°)
- θ2, diffraction peak position (°)
- $k_1$, form factor (k=0.9)
- $k_2$, Warren Form Factor constant (k=1.84)
- FWHM, width at half height of the corresponding diffraction peak (rad)

TABLE 3

X-Ray Diffraction parameters of GNFs and GMC-1

|  | Lc (nm) | La (nm) | d (nm) | npg |
|---|---|---|---|---|
| GNFs | 2.19 | 2.99 | 0.341740 | 6.4 |
| GMC-1 | 2.08 | 2.8 | 0.344338 | 6.05 |

When GNFs are transformed into GMC-1 the crystal structure of the material changes. In this way, a decreased of the crystal stack height (Lc), the in-plane crystallite size (La) and the number of graphene layers in the crystal (Nc) is observed in GMC-1 due to the purification, cleaning and exfoliation process to which the material has been subjected. The interlaminar space in GMC-1 increases due to the exfoliation process experimented in the material. Crystal stack height (Lc) and in-plane crystallite size (La) experiment a decreased due to the purification and exfoliation process.

Particle Size Distribution

The particle size distribution for the raw material GNFs and the product according to the invention GMC-1 was measured with a Mastersizer 3000 of Malvern Panalytical. The Mastersizer 3000 uses the technique of laser diffraction to measure the size of particles. It does this by measuring the intensity of light scattered as a laser beam passes through a dispersed particulate sample. This data is then analyzed to calculate the size of the particles that created the scattering pattern.

Figure 4A:
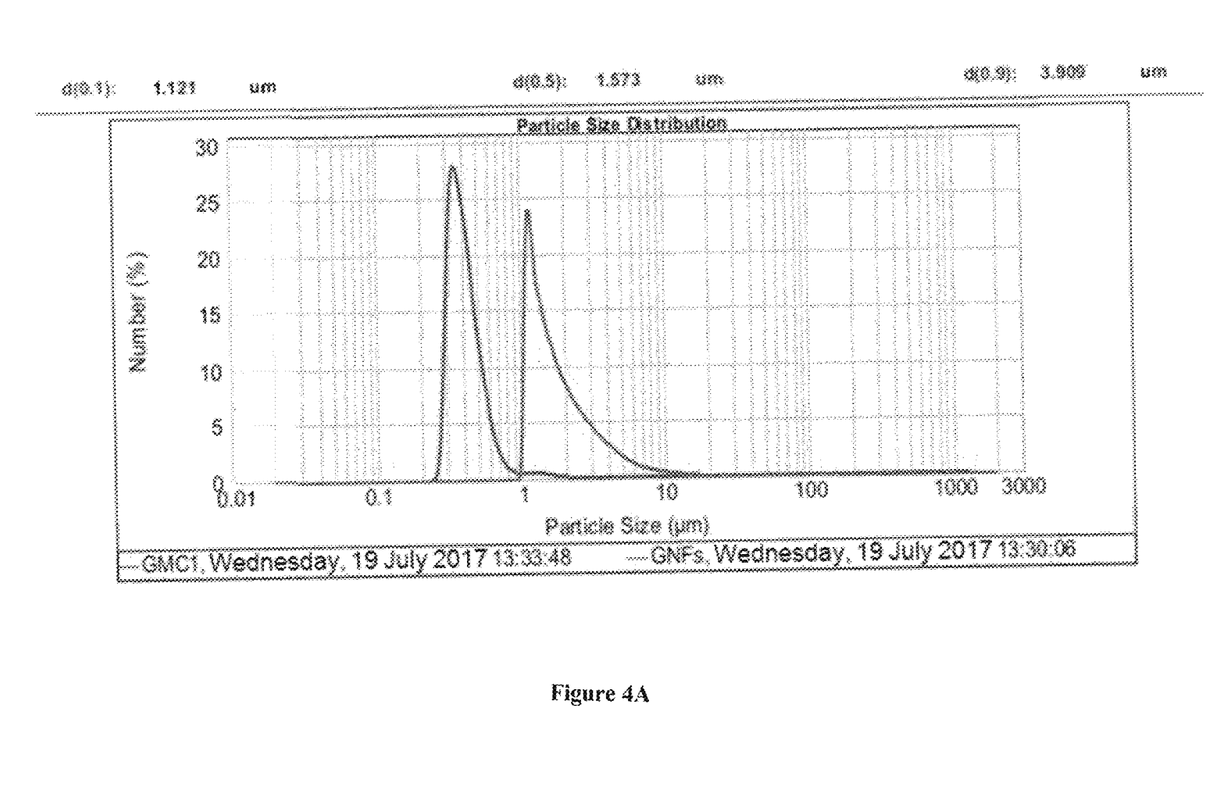
FIG. 4A.—Comparison of the particle size distribution in number of particles for GNFs raw material and GMC-1.

FIG. 4A shows the comparison of the particle size distribution in number of particles for GNFs and GMC-1.

Figure 4B:
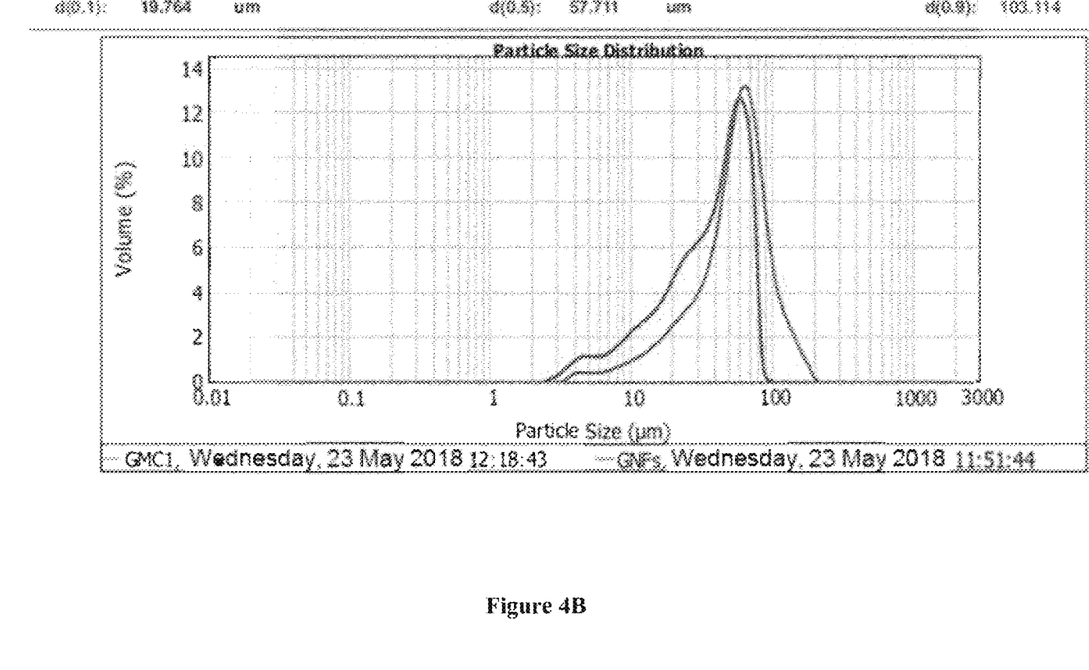
FIG. 4B.—Comparison of the particle size distribution according to the percentage of particle in volume of particles for GNFs raw material and GMC-1.

FIG. 4B shows the comparison of the particle size distribution according to the percentage of particle in volume of particles for GNFs and GMC-1.

The parameters d(0.1), d(0.5) and d(0.9) can be observed in the Figures, dn is referred to the number of particles and dv is referred to the volume in the particles.

For GNFs, dn(10) parameter means that the 10% of the number of particles have a size of 1.121 μm or smaller, dn(50) parameter means that the 50% of the number of particle have a size of 1.573 μm or smaller and dn(90) parameter means that the 90% of the number of particle have a size of 3.909 μm or smaller. For GNFs, dv(10) parameter means that the 10% of the volume of the sample is occupied by particles with a size of 19.764 μm or smaller, dv(50) parameter means that the 50% of the volume of the sample is occupied by particles with a size of 57.711 μm or smaller and dv(90) parameter means that the 90% of the sample is occupied by particles with a size of 103.114 μm or smaller.

In the case of GMC-1, dn(10) parameter means that the 10% of the number of particles have a size of 0.313 μm or smaller, dn(50) parameter means that the 50% of the number of particle have a size of 0.394 μm or smaller and dn(90) parameter means that the 90% of the number of particle have a size of 0.577 μm or smaller. For GMC-1, dv(10) parameter means that the 10% of the volume of the sample is occupied by particles with a size of 10.549 μm or smaller, dv(50) parameter means that the 50% of the volume of the sample is occupied by particles with a size of 39.693 μm or smaller and dv(90) parameter means that the 90% of the sample is occupied by particles with a size of 69.576 μm or smaller.

The comparison in particle size distribution in number and volume between GNFs and GMC-1 shows that GMC-1 has a lower particle size distribution. Summarizing, dn(90) for GNFs has a size of 3.909 μm or smaller for number of particle and a dv(90) of 103.114 μm or smaller for volume particle whereas dn(90) of GMC-1 has a size of 0.577 μm or smaller in number of particle and a dv(90) of 69.576 μm or smaller in volume particle. FIGS. 4A and 4B show clearly these reduction on number and volume of particle in GMC-1 as compared with the raw material used (GNFs).

Biological Activity

Statistics

The data shown are represented as the means±SEMs of a variable number of experiments. Student's t test was used for 2 samples and 1- or 2-way analysis of variance (ANOVA) was used for >2 samples, with a paired or unpaired design followed by a multiple comparison test. Values of P<0.05 were considered statistically significant.

Example 2: Toxicity Assays on HEP-G2 Cell Lines

We have performed tests with GMC-1 over cultured cells (hepatocyte line Hep-G2) used in pharmacological and toxicological studies.

In 6 wells culture dishes, 300,000 cells were seed per well and grown with 10% fetal bovine serum supplemented culture media (by default, DMEM). The cells were maintained under controlled incubator conditions of 37° C., 5% $CO_2$ and humidity. Once they reached confluence, they were deprived of serum for 16 hours. The product was added as suspension, at different concentrations keeping the same final volume for 24 hours in the same controlled maintaining conditions. Afterwards, the cells were processed and viability/toxicity were complementary tested by two tests pointed in the overmentioned ISO:

a) Trypan Blue exclusion, which differentiates live/dead cells and b) Metabolic activity by cellular dyeing with MTT (3-(4.5-dimethylthiazol-2-yl)-2.5-diphenyltetrazolium-bromid).

Figure 5:
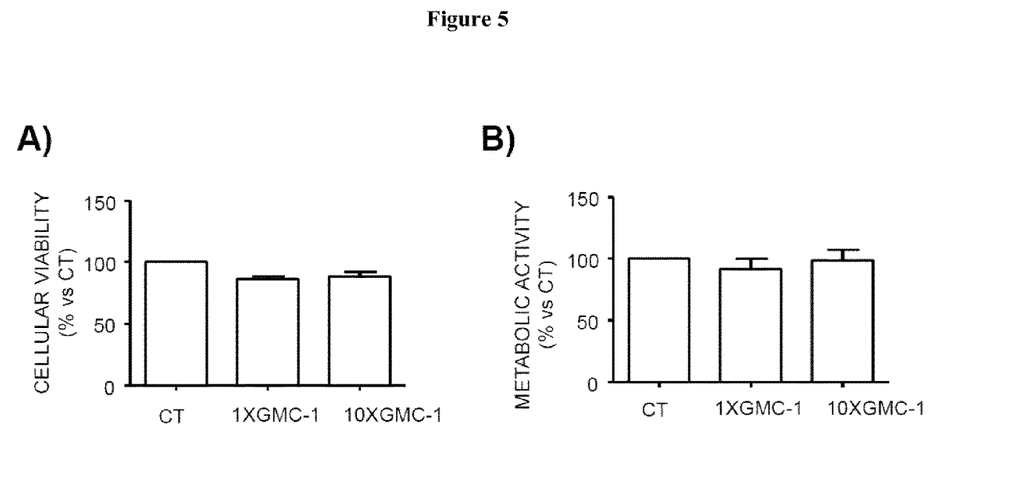
FIG. 5.—Toxicity assays in cultured Hep-G2 cells treated for 24 hours with GMC-1. A) Viability determined by trypan blue cellular exclusion and B) cellular metabolism determined by MTT with vehicle 1× and 10× concentration of GMC-1. The values are represented as mean+/−SEM.

The results are shown in FIG. 5. The data show that GMC-1 is non toxic on cultured Hep-G2 cell line.

Example 3: Wound Healing in Animal Model

Skin wound healing is a universal regenerative process to close the wound and reconstruct the epithelial barrier and the underlying connective tissue.

Many factors and systemic conditions are causative agents that compromise the dermal function. After injury to skin, a new epithelium has to form in order to close the wound.

Wound healing includes cell migration proliferation, differentiation, and extracellular matrix formation. Chronic wounds as venous, diabetic foot, or pressure ulcers are characterized by unresolved healing processes, including increased bacterial colonization and/or infection, and they are caused by other conditions and diseased, such as diabetes mellitus, trauma, inflammatory diseases, metabolic abnormalities, bleeding disorders, smoking, immunosuppression, malnutrition and obesity.

We performed dermal regeneration assays in a rodent model of wound healing. The formulation of GMC-1 was based in a hydrogel with gelatin as main excipient component [X. J. Yang, et al., Polym. Int. 44 (1997) 448-452].

The animal model used is *Rattus norvegicus*, male or female, 3-8 months old between 300-500 body weight at the beginning of the experiments, n=18). Rats were divided in 2 groups, treated with a formulation that contains the product or the same formulation without it. The animals were anesthetized with isoflurane and the dorsal skin was shaved. After sanitizing with 70% ethanol, 5 thickness wounds were created on the dorsal skin using 4-mm-diameter dermal biopsy punches. 4 of the wounds were treated with a patch based in a formulation that comprises GMC-1 or not (control). The 5th biopsy was left uncovered as a control of closure. The formulation is applied each second day. The wound closure was monitored over time by planimetric measurement, in which photographs of each wound, using a digital camera (PowerShot Prol, Canon) were taken at 0-2 and 4 days after injury. Wound area was analyzed (JImage, NIH). The percentage of wound closure at each time point was derived by the following formula: (1−[current wound size/initial wound size])×100. This value is percentaged versus the 5th biopsy closures value (inner control of the animal).

On the 4th day, the animals were sacrificed and the area of the wound healed were excised, fixed in 10% neutralized formaldehyde for 24 h and embedded in paraffin. Three μm thickness sections were dewaxed in xylene and rehydrated by successive immersion in descending concentrations of ethanol and histopathological determinations (re-epithelitation, collagenization and acute inflammatory infiltration) were achieved. The epithelitation of each wound was scored based in the individual scores determined by the histopathological analysis commented above.

Figure 6:
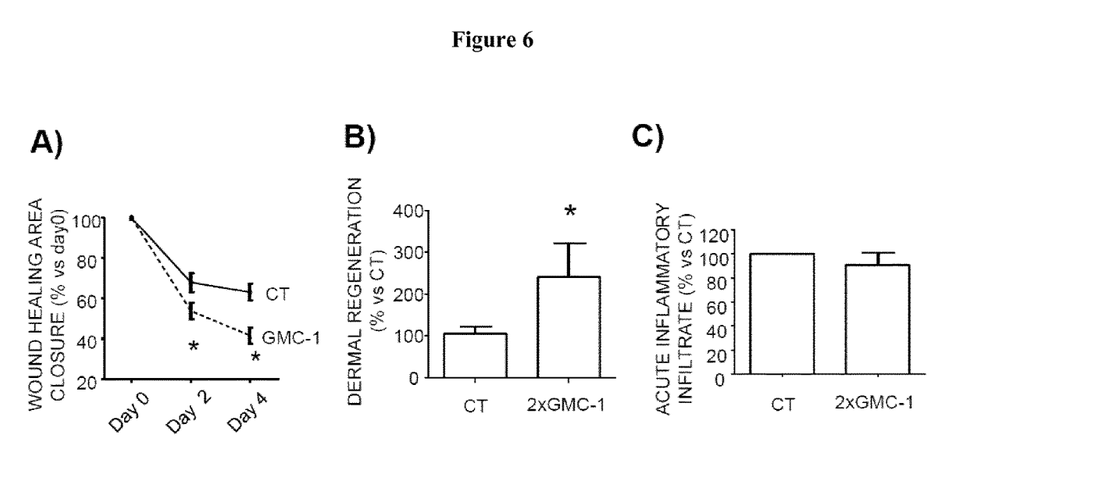
FIG. 6.—Dermal wound healing rodent model (*Rattus Norvegicus*), based on biopsies achieved over the dorsal area, were topically treated every 2 days with a formulation which includes 2× GMC-1 or not (CT). A) Wound area closure time-course, B) dermal regeneration (collagenization and re-epithelitation) and C) acute inflammatory infiltrate at the 4th day. The values are percentaged against the inner control wound per animal (not treated with any formulation) and represented as mean+/−SEM. *=P<0.05 vs. CT, value considered statistically significant.

The results are shown in FIG. 6. Topically applied GMC-1 regenerates the dermis in vivo.

After the euthanasia, the plasmas and the periphery blood mononuclear cells (the main leucocyte population circulating in the blood) were preserved and studied. A general biochemistry of the plasmas was achieved and different renal, hepatic and inflammation markers were studied (creatinine, transaminases and wide range C-reactive protein between others). The PBMCs were manipulated to study the expression of the pro-inflammatory marker Interleukin 1-beta. This expression change was determined using Reverse transcription-quantitative polymerase chain reaction (RT-qPCR). 100 ng of converted DNA (cDNA) of the original mRNA extracted from the different samples were amplified with commercial gene expression assays (TaqMan, Life Technologies). The values were normalized against an endogenous control (beta-actin) and then the fold change in the expression was performed using the method 2^-deltadeltaCt.

Figure 7:
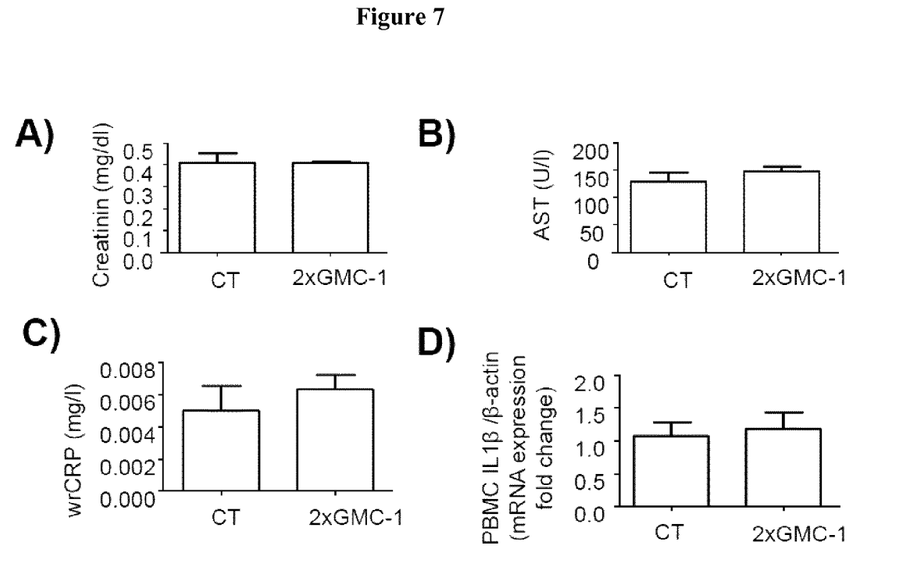
FIG. 7.—Systemic biochemical analysis of a dermal wound healing rodent model (*Rattus Norvegicus*), based on biopsies achieved over the dorsal area, treated topically every 2 days with a formulation which includes 2× GMC-1 or not (CT). At the 4th day and after euthanasia, the plasmatic A) creatinine, B) aspartate aminotransferase (AST) and wrCRP (wide range C-reactive protein) were determined. D) In peripheric blood mononuclear cells (PBMC), the mRNA expression fold change was determined by RT-qPCR for systemic inflammatory marker the Interleukin 1-beta (IL-1-beta) expression. The values are represented as mean+/−SEM.

Results are shown in FIG. 7. Topically applied GMC-1 over a skin wounded area is harmless in terms of systemic changes of renal, hepatic or inflammatory markers in vivo.

The invention claimed is:

1. A graphene nanomaterial consisting of particles of purified graphene nanofibers, wherein the particles have a particle size distribution wherein 90% of the particles as measured by number of particles have a diameter of 0.60 μm or smaller and 90% of the particles as measured by volume of particles have a diameter of 80.00 μm or smaller, as measured by a laser diffraction method.

2. The graphene nanomaterial according to claim 1, wherein a specific surface area of the graphene nanomaterial is between 100 and 500 $m^2/g$ as measured by the Brunnauer-Emmet-Teller method.

3. The graphene nanomaterial as defined in claim 2, wherein the specific surface area is between 300 and 350 $m^2/g$ as measured by the Brunnauer-Emmet-Teller method.

4. The graphene nanomaterial as defined in claim 1, wherein the graphene nanomaterial has a pore volume between 0.35 and 0.40 $cm^3/g$.

5. The graphene nanomaterial as defined in claim 1, wherein the graphene nanomaterial has a specific surface area between 300 and 350 $m^2/g$ as measured by the Brunnauer-Emmet-Teller method and a pore volume between 0.35 and 0.40 $cm^3/g$.

6. The graphene nanomaterial according to claim 1, wherein impurities in the nanomaterial are present in an amount of less than 0.01% by weight.

7. A pharmaceutical composition comprising the graphene nanomaterial as defined in claim 1 and a pharmaceutically acceptable excipient.

8. The pharmaceutical composition according to claim 7, wherein the pharmaceutical composition is in a form selected from the group consisting of a cream, an ointment, a microemulsion, a gel, an emulsion-gel, a paste, a foam, a tincture, a patch, a bandage, a membrane, a matrix and a transdermal delivery system.

9. The pharmaceutical composition according to claim 8, wherein the composition is in the form of a hydrogel or a cream.

10. A method for preparing the graphene nanomaterial according to claim 1 from a raw graphene material comprising particles of raw graphene nanofibers, the method comprising the steps of:
   a) purifying the raw graphene material to remove any metal or impurity present in the raw graphene material to obtain purified graphene nanomaterial; and
   b) reducing a particle size of the purified graphene nanomaterial, to a particle size distribution wherein 90% of the particles as measured by number of particles have a diameter of 0.60 μm or smaller and 90% of the particles as measured by volume of particles of have a diameter of 80.00 μm or smaller, as measured by a laser diffraction method.

11. The method according to claim 10, wherein the step of purifying takes place using an acid selected from the group consisting of $H_2SO_4$, HCl, HF, $HNO_3$ and HBr.

12. The method according to claim 10, wherein the step of reducing a particle size of the purified graphene nanomaterial takes place using an exfoliation process at room temperature.

13. The method according to claim 10, further comprising the step of subjecting the graphene nanomaterial obtained in step (b) to a depyrogenization process at 200-500° C. for 10-60 min.

* * * * *